United States Patent [19]

Suga et al.

[11] Patent Number: 5,305,634
[45] Date of Patent: Apr. 26, 1994

[54] WEATHERING TEST METHOD AND SAMPLE HOLDER USED THEREIN

[75] Inventors: Shigeru Suga; Shigeo Suga; Etsuji Natori, all of Tokyo, Japan

[73] Assignee: Suga Test Instruments Co. Ltd., Tokyo, Japan

[21] Appl. No.: 982,372

[22] Filed: Nov. 25, 1992

[51] Int. Cl.$^5$ ............................................. G01N 17/00
[52] U.S. Cl. ............................................. 73/86; 73/856; 73/865.6
[58] Field of Search ............... 73/86, 87, 760, 785, 73/788, 796, 797, 806, 812, 813, 818, 826, 833, 856, 865.6

[56] References Cited

U.S. PATENT DOCUMENTS

| | | | |
|---|---|---|---|
| 2,270,389 | 1/1942 | Straus et al. | 73/86 |
| 3,504,535 | 4/1970 | Cobb et al. | 73/86 |
| 3,922,903 | 12/1975 | Bornstein et al. | 73/86 |
| 4,566,335 | 1/1986 | Singhal | 73/856 |
| 4,704,903 | 11/1987 | Suga et al. | 73/865.6 |

FOREIGN PATENT DOCUMENTS 64-35346 6/1989 Japan .

OTHER PUBLICATIONS

Japanese publication: Japanese Industrial Standard JIS D 0205, 1987.
Japanese publication: Japanese Industrial Standard JIS Z 8730, 1980.

*Primary Examiner*—Donald O. Woodiel
*Attorney, Agent, or Firm*—Wenderoth Lind & Ponack

[57] ABSTRACT

A weather-fastness test method utilizing a novel sample holder and constituted by the steps of fixing the sample to the holder which is provided with metal coils the shape of which varies in accordance with the variation in the temperature of the ambient air and the radiation heat from a light source and which are connected so as to apply a force to the sample as the temperature changes, placing the sample under predetermined conditions, e.g. exposing the sample to radiation by light, to air having a temperature and humidity of predetermined levels, and to rain, while the sample is under repeated tension, compressive force and/or bending stress due to the variation of the shape of the coils and imparted to the sample, and then evaluating the weather-fastness resistance of the sample.

32 Claims, 6 Drawing Sheets

WEATHERING TEST METHOD AND SAMPLE HOLDER USED THEREIN

This invention relates to a weathering, or weather-fastness, test method carried out under predetermined conditions, e.g. exposing a sample to light, to air having a temperature and humidity of predetermined levels, and to rain, and while the sample is under tension, compressive force and/or bending stress is repeatedly imparted thereto; and to a sample holder used in such a method.

BACKGROUND OF THE INVENTION

Figure 4:
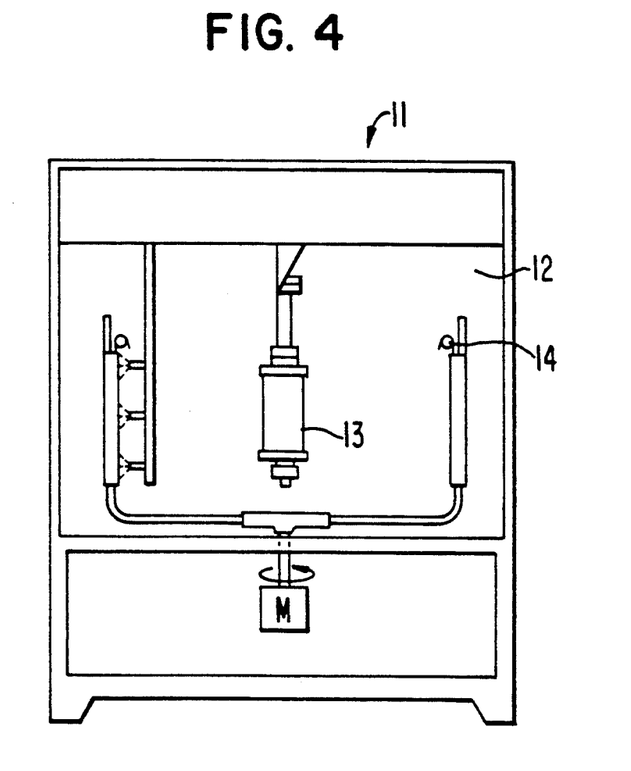
FIG. 4 is a front elevation view of a generally-used accelerated weather-fastness test machine.

The weathering tests which have heretofore generally been conducted include such tests known as an accelerated weather-fastness test, which is a test carried out in a laboratory under predetermined conditions, e.g. exposing a sample, placed in an enclosure similar to the environment in which it is to be used, to the radiation of light, to air having a temperature and humidity of predetermined levels, and to rain in an accelerated weather-fastness testing machine such as is shown in FIG. 4, and atmospheric exposure tests carried out by placing a sample directly in a natural outdoor environment.

The accelerated weather-fastness testing machine 11 shown in FIG. 4 is used in a weather-fastness test conducted by placing a light source 13 in the central portion of a test chamber 12, attaching a sample 15 to a holder 16 (for example, the holder shown in FIG. 5A) in an unstressed state, i.e. without any tension, compressive force or bending stress applied thereto, and having the holder 6 on a sample frame 14 adapted to be rotated around the light source 13.

Figure 5A:
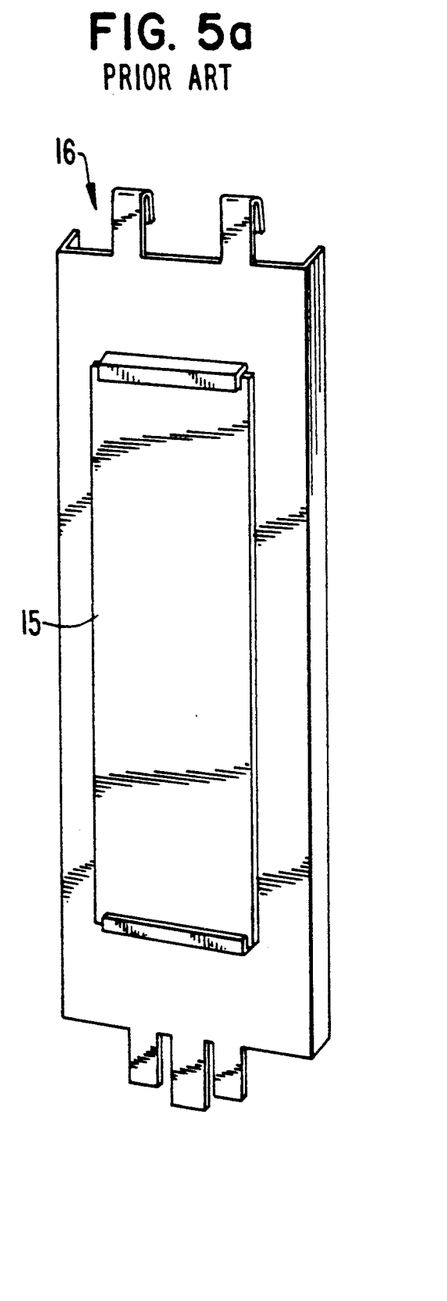
FIG. 5a is a perspective view of a conventional holder used in a conventional weather-fastness test such as is shown in FIG. 4.
Figure 5B:
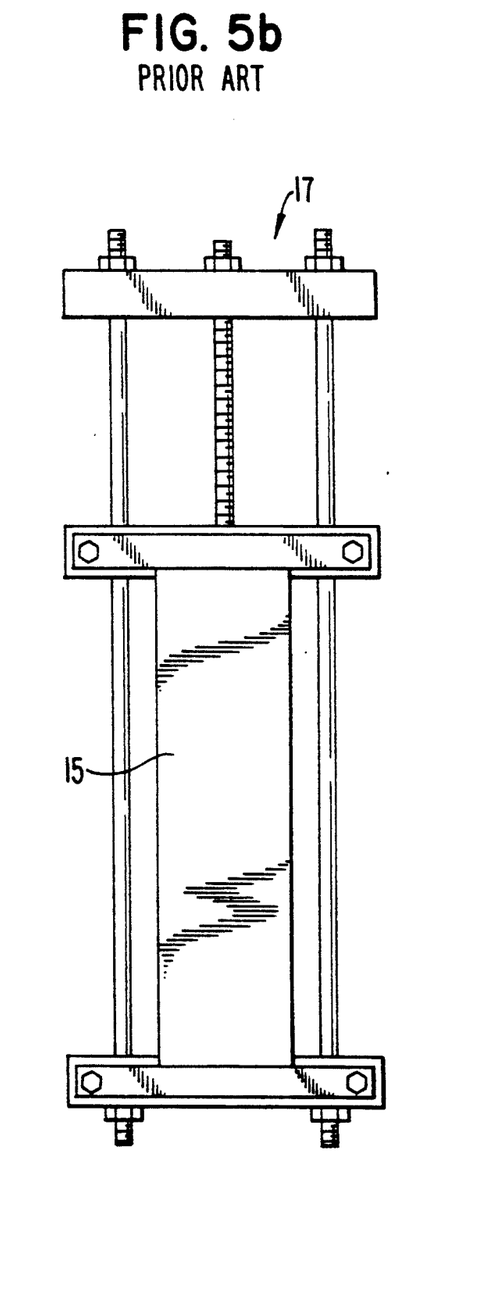
FIG. 5b is a front elevation view of another conventional holder.

A weather-fastness test method as disclosed in Japanese Patent Laid-Open Application No. 35346/1989, is carried out by using a holder 17 as shown in FIG. 5B, by which stress (e.g. tensile stress) of a predetermined level is constantly and positively imparted to a sample 15. The outdoor exposure test methods shown and described, for example, in JIS D 0205, include a method carried out on a rubber-like sample exposed as it is, and a method carried out by using a rubber-like sample bent in a looped state under bending stress of a predetermined level constantly and positively imparted thereto.

These weather-fastness tests which have heretofore generally been conducted are carried out with a sample in a static state, i.e. in a state in which stress is not imparted to the sample, or in a dynamic state in which stress of a predetermined level is constantly imparted to the sample.

A weather-fastness test method requires that: (1) the deteriorated condition of a sample have some correlation with the deteriorated condition which would be seen if the sample were subjected to exposure in its intended condition of use, i.e. outdoors; (2) the method be highly accelerated in comparison with an atmospheric exposure test method which places the sample in its intended condition of use; and (3) the tests conducted be repeatedly under the same conditions and be reproducible.

Many materials and products in practical use are under tensile stress, compressive stress and/or bending stress at all times. Since the force generating such stress generally varies with temperature, the level of stress imparted to the materials and products is not always constant, but rather it varies as the temperature varies. For example, the temperature of a material used as an interior facing material for an automobile varies repeatedly in accordance with the variation of the outdoor temperature. Since the temperature inside an automobile due to the outdoor temperature can increase as much as 100° C. in the daytime and drop to 20° C. in the nighttime, the level of stress imparted to the material also varies.

However, a conventional weather-fastness test method, which is used to test a sample in a static or dynamic state as described previously, does not test a sample by reproducing the repetition of variation of the stress generation force imparted to the materials and products to which they are subjected during their intended use.

Therefore, in a test using an accelerated weather-fastness test method, the deteriorated condition of a sample placed in its intended condition of use may not be accurately reproduced, so that the deteriorated condition of a sample tested in such a machine may have little correlation with that of a sample placed in its intended condition of use. Since the variation of stress is taken into consideration in any test conducted under actual conditions of use, it is necessary that a material or product to be placed in practical use be tested under the conditions of such use in any testing method. This requires a large space for carrying out such tests, and the expenditure of a lot of money.

OBJECT AND BRIEF SUMMARY OF THE INVENTION

There has therefore been a strong demand for a test method capable of solving these problems, and it is an object of the present invention to provide such a method and a sample holder used in this method.

To this end, the present invention provides a weather-fastness test method utilizing a novel sample holder and comprising the steps of fixing the sample to the holder which is provided with metal coils the shape of which varies in accordance with the variation in the temperature of the ambient air and the radiation heat from a light source and which are connected so as to apply a force to the sample as the temperature changes, placing the sample under predetermined conditions, e.g. exposing the sample to radiation by light, to air having a temperature and humidity of predetermined levels, and to rain, while the sample is under repeated tension, compressive force and/or bending stress due to the variation of the shape of the coils and imparted to the sample, and then evaluating the weather-fastness resistance of the sample.

BRIEF DESCRIPTION OF THE DRAWINGS

The invention will now be described in greater detail in connection with the accompanying drawings, in which.

DETAILED DESCRIPTION OF THE INVENTION

In its intended environment, a seat material for automobiles, for example, is mounted in a tensile stressed state, i.e. in a stretched state, in the interior of an automobile. When the seat material then is subjected to sunlight, it is further stretched due to the radiation of the sunlight and an increase in the ambient temperature within the automobile. Consequently, the seat material expands, and the light, air, temperature and humidity work on the material to accelerate the deterioration of the material. Moreover, the seat material expands and contracts repeatedly in accordance with the variation of the temperature, so that an aging phenomenon occurs therein more readily than in a similar material in a static or in a state under a steady stress.

The weather-fastness test method according to the present invention is a method for reproducing these phenomena experimentally, and is capable of conducting an accelerated exposure test in an environment like the environment of the intended use of the material being tested by using a miniaturized sample and under the same conditions as in a test using an actual product in the intended condition of use.

In this method, a sample is attached to a sample holder provided with coils made of a material, such as metal, such that the shape of the coils varies in accordance with the variation of temperature. Thus, stress is imparted to the sample owing to the variation in the shape, i.e. expansion and contraction, of these coils. When the ambient temperature and the temperature due to the radiation heat of the light vary, the shape of the coils varies, so that the level of stress imparted to the sample being held also varies repeatedly in accordance with the repeated variation of the temperature in the same manner as the level of stress of a material or a product in practical use in its intended environment varies.

A specific example of a preferred embodiment of the present invention will now be described with reference to the drawings.

Figure 1A:
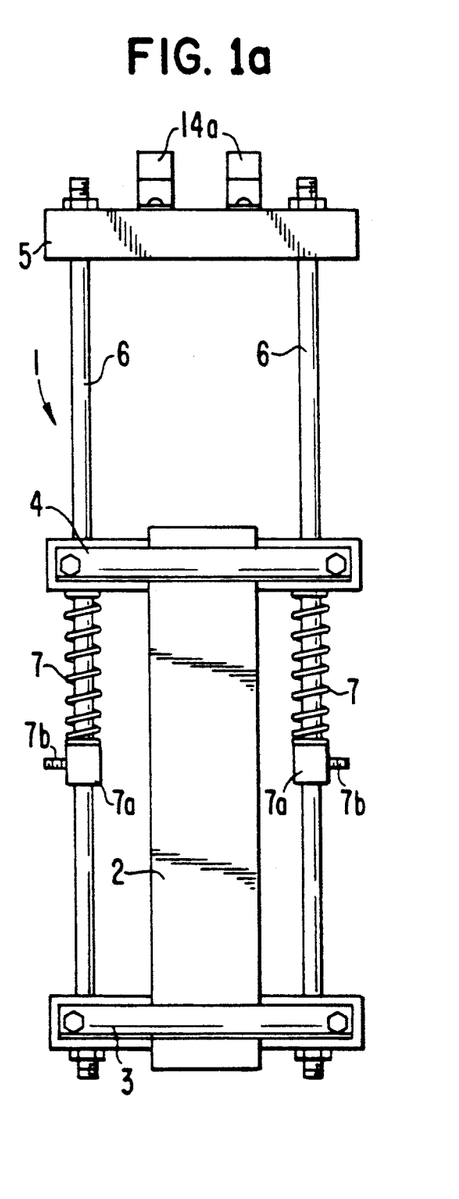
FIG. 1a is a front elevation view of a sample holder used in the present invention and adapted to impart tensile stress to a sample and showing the holder with a sample in an unstressed state.
Figure 1B:
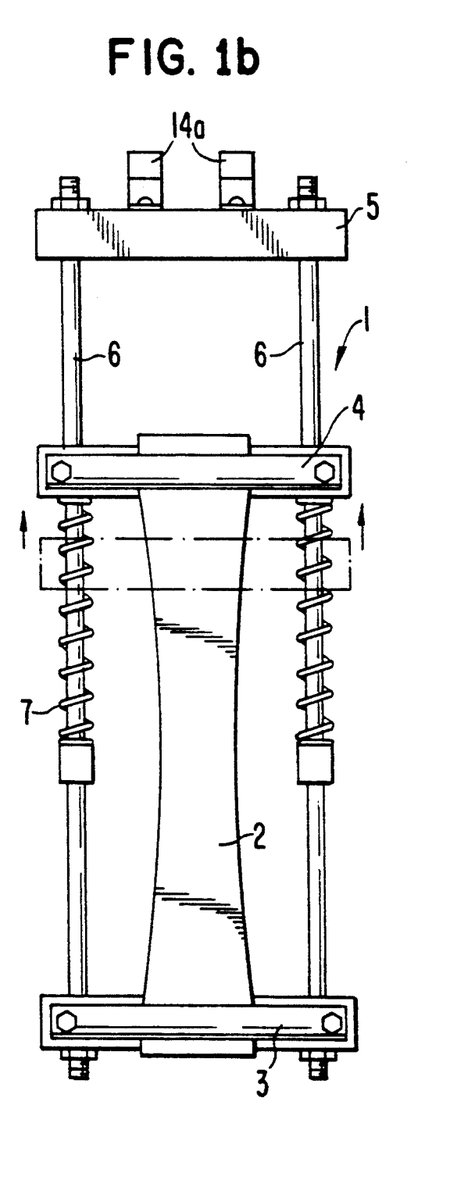
FIG. 1b is a similar view of the holder of FIG. 1a with the sample under tensile stress.

FIGS. 1a and 1b show a first embodiment of a sample holder used in the present invention. This holder 1 consists of a fixed sample holding member 3 for holding one end of a sample 2 in a vertically extended state and a movable sample holding member 4 holding the other end of the sample 2, two parallel slide rods 6 held firmly at both end portions thereof by the fixed sample holding member 3 and a metallic connecting member 5 and having portions of the movable sample holding member 4 which are close to the ends thereof slidable on the rods 6. Metal coils 7 are mounted around the slide rods 6 and have one end in contact with the movable sample holding member 4 and extend between the fixed and movable sample holding members 3 and 4. In this embodiment, the other end of each coil is fixed by engagement with a stop 7a held on a corresponding slide rod 6 by a set screw 7b.

The coils 7 expand and contract linearly in a predetermined range of temperature, for example, in the range of 20°–70 C. These coils 7 expand to a maximum length at a temperature of, for example, 70° C., and return to their original length at a temperature of, for example, 20° C.

The holder 1 is suitable for use in a tensioning fatigue test on an expansible material, such as rubber and fiber material.

A weather-fastness test on a sample 2 mounted on the holder 1 is conducted as follows. The holder 1 preferably has the sample 2 mounted between the fixed sample holding member 3 and the movable sample holding member 4 in an environment in which the coils are at the zero expansion condition, in this case 20° C. The holder is then mounted on a sample frame 14 in, for example, an accelerated weather-fastness test machine 11 as shown in FIG. 4, by means of hooks 14a on the holder. Since the temperature in the test chamber 12 varies according to the operations of regulating the temperature in this chamber as well as operations of turning a light source on and off and an operation of spraying water on the sample, the coils 7 expand and contract repeatedly due to this variation of temperature. The coils 7 expand and contract between the minimum length and an extended length while acting to increase the tension on the sample 2 in proportion to the increase in temperature. This causes a repeated predetermined level of tensile stress to be imparted to the sample 2 with the generation force being varied as the coils expand and contract, as the weather-fastness test is being conducted.

If the holder 1 is used in an outdoor exposure test, the coils 7 also expand and contract repeatedly due to, for example, the difference in temperature in daytime or nighttime. This causes repeated tensile stress to be imparted to a sample with the generation force being varied as the coils expand and contract, in the same manner as in the test using the same holder in the above-described accelerating weather-fastness test machine, as the weather-fastness test is being conducted.

It will be understood, however, that the sample can be mounted in a non-tensioned condition in an environment in which the temperature is slightly elevated from the zero expansion condition, but this will not permit tensioning the sample over the full range of expansion of the coils, and if the coils and sample are cooled below the temperature at which the sample was mounted, this may apply a compression to the sample. Further, the holder 1 can be used to apply a compression force to the sample 2. If the sample 2 is mounted in an environment with a high temperature at which the coils 3 are fully or substantially fully expanded, or if the temperature in the test chamber is caused to fall, the coils 7 contract and apply a compressive force to the sample 2.

If the coils 7 are made of a material which contracts as it is heated, the holder will operate reversely from the manner described above. For example, if a sample 2 is mounted at a lower temperature, when the temperature increases, the coils 7 will contract and exert a compressive force on the sample.

Figure 2A:
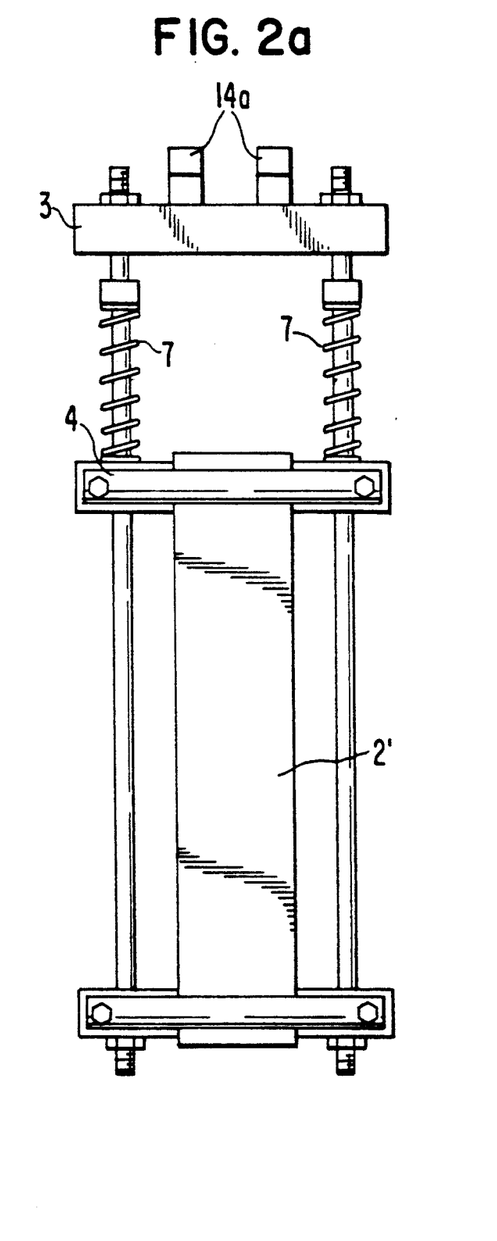
FIG. 2a is a front elevation view of a sample holder used for imparting compressive stress to a sample and showing the holder with the sample in an unstressed state.
Figure 2B:
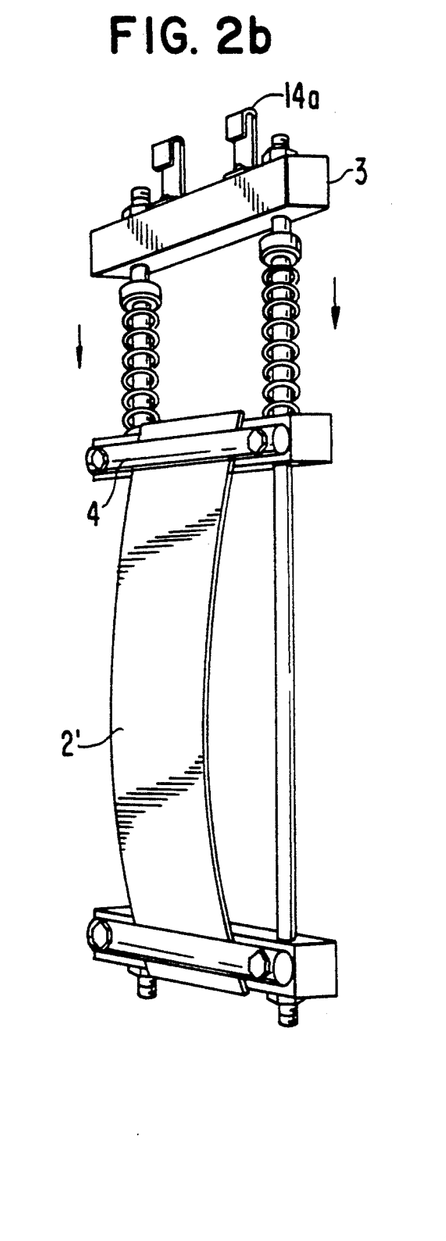
FIG. 2b is a similar view of the holder of FIG. 2a with the sample under compressive stress.

FIGS. 2a and 2b show a different embodiment of a holder 1' for use in imparting compressive or bending stress to a sample 2' by using coils 7' which expand when heated, similar to those described in connection with FIGS. 1a and 1b. The holder 1' is the same as the holder 1 of FIGS. 1a and 1b except that the coils 7' are engaged with a movable sample holding member 4 and extend between the movable sample holding member 4 and the metallic connecting member 5.

The holder 1' is preferably used in a case where a weather-fastness test is to be performed on a material having a low expansibility, such as a plastic plate or a coated plate. In such a case, when the sample is mounted at a low temperature, the coils 7 expand and contract in the same way as described above, but repeatedly impart increasing compressive stress to the sample 2' as the temperature rises, and the generation force is varied as the weather-fastness test is conducted. As with the embodiment of FIGS. 1a and 1b, by loading at a high temperature, the holder will exert a tensile stress on the sample as the temperature falls. Similarly, by changing the coils to a material which contracts when it is heated causes the holder to operate in the reverse manner.

The sample 2' as shown is, because it is so thin, actually bent by the action of the compressive force on the ends thereof. Thus, for a particular type of specimen, the holder can be used to apply repeated bending stress.

Figure 3A:
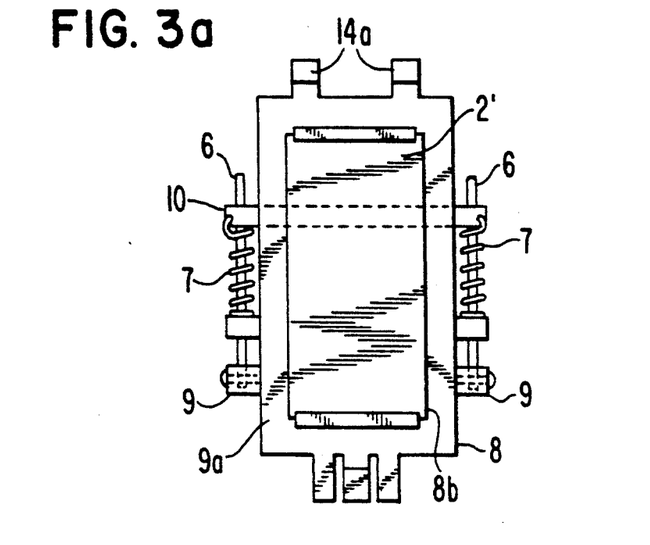
FIG. 3a is a front elevation view of a sample holder for imparting bending stress to a sample and showing the holder with the same in the unstressed state.
Figure 3B:
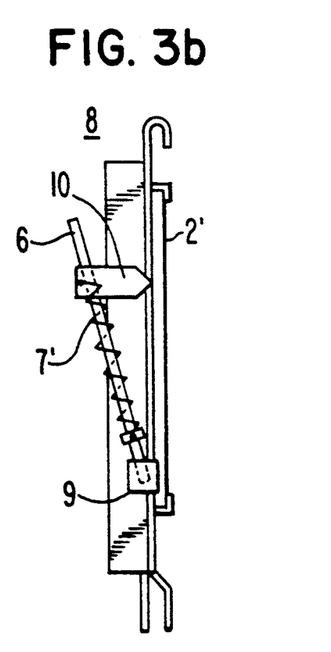
FIG. 3b is a side elevation view thereof.
Figure 3C:
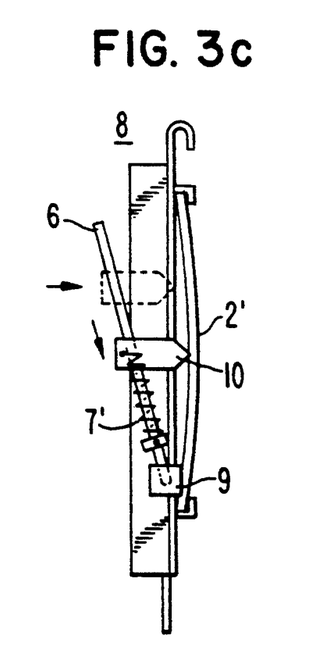
FIG. 3c is a similar view of the holder of FIG. 3b with the sample under bending stress.

FIGS. 3a-3c show another embodiment of a holder 8 for use in imparting stress to a sample, such as a plastic material or a coated material. The holder 8 has a rectangular frame 8a provided with an opening 8b in the central portion thereof. A sample 2' is mounted on the front surface of this holder, and slide rods 6 are fixedly mounted by metallic mounting members 9 to the opposite side surfaces of the holder frame 8a so that the slide rods 6 can incline rearwardly of the frame at a predetermined angle in planes parallel to the side surfaces. Coils 7' similar to those described in connection with the embodiments of FIGS. 1a and 1b and FIGS. 2a and 2b but which contract as the temperature rises, are provided around the slide rods 6, and fixed at the end portions thereof which are toward the metallic mounting members 9 on the slide rods 6, and at the other end portions thereof to end portions of a metallic sample-bending member 10 slidable on rods 6. The metallic sample-bending member 10 consists of a bar the cross section of which is a square portion with a triangular portion projecting toward the sample with the apex of the triangular portion of this member contacting the rear surface of the sample 2'.

The coils 7' on this holder 8 are made of a material which contracts and expands repeatedly with the increase and decrease of the temperature. As these coils 7' expand and contract, the metallic sample-bending member 10 is moved upwardly and downwardly along the slide rods 6 and the apex of the member 10 which contacts the rear surface of the sample 2' is moved vertically on the sample surface. Consequently, stress, the level of which corresponds to the angle at which the slide rods 6 are fixed and the position of the sample-bending member 10, is imparted as bending stress to the sample 2' from the rear surface thereof with the stress increasing as the temperature rises so as to contract the coils 7'. Accordingly, a weather-fastness test can be conducted by repeatedly imparting bending stress to the sample with the generation of the force for causing the stress to be varied in the same manner as in the holders described in connection with FIGS. 1a and 1b and FIGS. 2a and 2b. As with the holders of FIGS. 1a-2b, the coils 7' of the holders of this embodiment can be placed above the sample bending member, or the sample can be mounted in a high temperature environment or the material of the coils 7' can be changed to one which expands when heated, and the different modes of operation can be obtained as with the holders of FIGS. 1a-2b.

Figure 6:
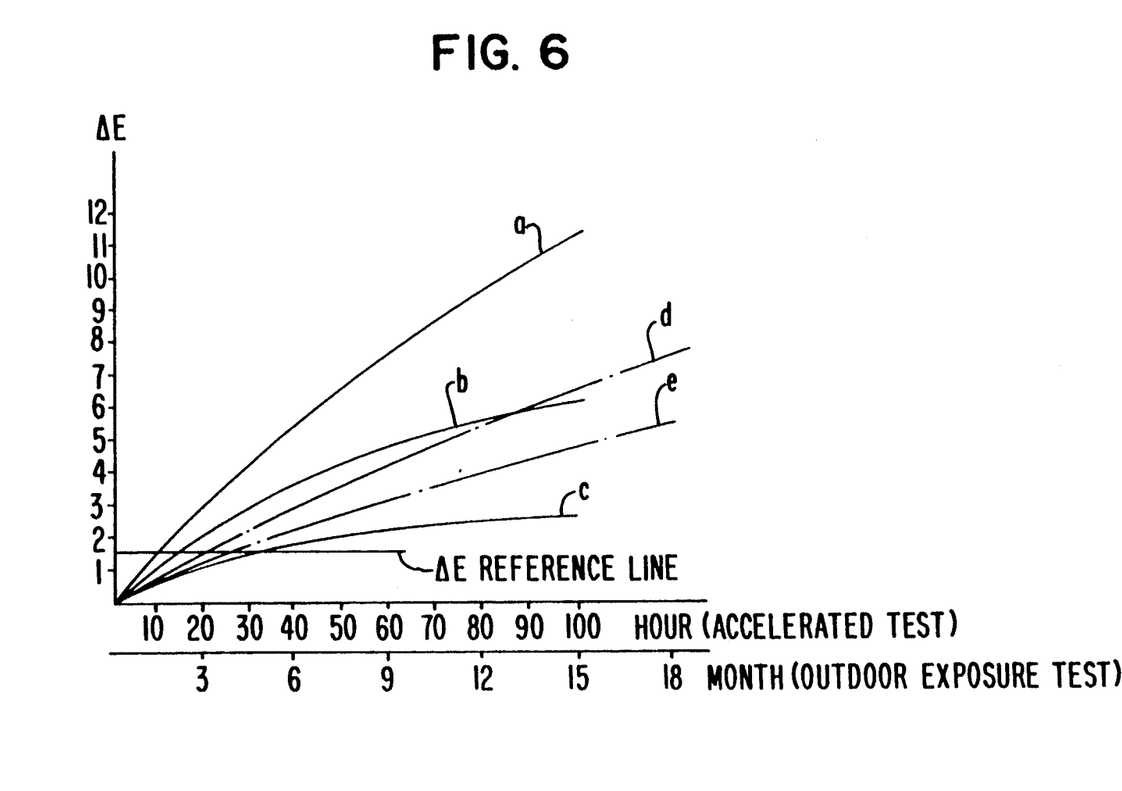
FIG. 6 is a graph showing the results of weather-fastness tests conducted on a polyester seat material for automobiles.

FIG. 6 shows the results of accelerated weather-fastness tests conducted in a polyester seat material for an automobile. Referring to the figure, curves a, b, c, for which the time scale is hours, represent the results of weather-fastness tests conducted by using the accelerated weather-fastness test machine shown in FIG. 4 with various holders, and curves d, e, the time scale for which is months, the results of outdoor exposure tests. Table 1 shows the test conditions under which the tests to produce the data for curves a, b and c were conducted, in which a represents the test method according to the present invention, and b and c conventional test methods.

TABLE 1

| | Test Conditions Corresponding to the Curves a, b, c | | |
|---|---|---|---|
| Curve | Test Temperature °C. | Light source lighting conditions | Holder used |
| a | 63 | Brightness cycle | FIG. 1 |
| b | 63 | Continuous irradiation (Constant lighting) | FIG. 5b |
| c | 63 | Brightness cycle | FIG. 5a |

(Note 1) A black enamel-coated black panel thermometer was set in the same position as the sample surface so that the maximum temperature of the sample surface could be measured as a test temperature.
(Note 2) In the brightness cycle, a 3.8-hour light source lighting period and a one-hour lights-out period were alternately repeated.

The curve d shows the results of an outdoor exposure test conducted with a sample attached to the holder of FIG. 1, and the curve e the result of an outdoor exposure test conducted with a sample attached to the holder of FIG. 5a.

A comparison of the curves of FIG. 6 shows:
(1) the method a can accelerate the testing to about three times as fast as that of c;
(2) the method d can accelerate the testing to about one and a half times as fast as that of e;
(3) in methods a, d and e, $\Delta E$, namely the color difference as measured according to JIS 28730-1980, increases substantially linearly with the passage of time. Accordingly, these results have good correlation;
(4) unlike the graphs referred to in (3) above, b and c are not in good correlation with d and e.

As is clear from the above, the weather-fastness test method according to the present invention accelerates the tests to two to three times as fast as that of a conventional accelerated weather-fastness test method, and is well correlated with an outdoor exposure test method. Moreover, in the outdoor exposure test, the test can accelerate to about one and one-half times as fast as that of a conventional outdoor exposure test, and a complete article with the material to be tested thereon in its intended form is not required for exposure, so that a large space to carry out exposure is unnecessary. Accordingly, the expenses can be cut down greatly in all cases, i.e. economical tests can be conducted.

What is claimed is:

1. A method for carrying out a weathering test on a sample, comprising:

providing a sample holder having a fixed sample holding member for holding one end of a sample to be tested, a movable sample holding member for holding the other end of the sample to be tested, a movable sample holding member mounting means on which said movable sample holding member is movably mounted for movement toward and away from said fixed sample holding member, and a force applying means made of a material which is expandable and contractable by a predetermined amount with variations in temperature over a predetermined range and which is engaged with said movable sample holder;

mounting a sample in said holder by connecting respective ends of the sample to said fixed and movable sample holding members;

positioning said holder in an environment under weather conditions corresponding to those for which the sample is to be tested and including repeatedly varying temperature varying in a range of temperatures in which said force applying means expands and contracts for exposing said sample to said weather conditions while applying varying force to said sample by the expansion and contraction of said force applying means in accordance with the variations in temperature; and evaluating the weather-fastness of the thus tested sample.

2. A method as claimed in claim 1 in which said material is a material which expands as temperature increases and contracts as temperature decreases, and which is engaged with said movable sample holding member for moving said movable sample holding member away from said fixed sample holding member as said material expands, and said step of mounting is carried out at a temperature in a lower portion of the range of temperatures for applying tension to the sample as the temperature increases and said material expands followed by relieving tension as the temperature decreases and said material contracts.

3. A method as claimed in claim 1 in which said material is a material which expands as temperature increases and contracts as temperature decreases, and which is engaged with said movable sample holding member for moving said movable sample holding member away from said fixed sample holding member as said material expands, and said step of mounting is carried out at a temperature in a higher portion of the range of temperatures for applying compressive force to the end of the sample held in said movable holding member as the temperature decreases and said material contracts followed by relieving compressive force as the temperature increases and said material expands.

4. A method as claimed in claim 1 in which said material is a material which expands as temperature increases and contracts as temperature decreases, and which is engaged with said movable sample holding member for moving said movable sample holding member toward said fixed sample holding member as said material expands, and said step of mounting is carried out at a temperature in a lower portion of the range of temperatures for applying compressive force to the end of the sample held in said movable holding member as the temperature increases and said material expands followed by relieving compressive force as the temperature decreases and said material contracts.

5. A method as claimed in claim 1 in which said material is a material which expands as temperature increases and contracts as temperature decreases, and which is engaged with said movable sample holding member for moving said movable sample holding member toward said fixed sample holding member as said material expands, and said step of mounting is carried out at a temperature in a upper portion of the range of temperatures for applying tension to the end of the sample held in said movable holding member as the temperature decreases and said material contracts followed by relieving tension as the temperature increases and said material expands.

6. A method as claimed in claim 1 in which said material is a material which contracts as temperature increases and expands as temperature decreases, and which is engaged with said movable sample holding member for moving said movable sample holding member away from said fixed sample holding member as said material expands, and said step of mounting is carried out at a temperature in a lower portion of the range of temperatures for applying a compressive force to the sample as the temperature increases and said material contracts followed by relieving of compressive force as the temperature decreases and said material expands.

7. A method as claimed in claim 1 in which said material is a material which contracts as temperature increases and expands as temperature decreases, and which is engaged with said movable sample holding member for moving said movable sample holding member away from said fixed sample holding member as said material expands, and said step of mounting is carried out at a temperature in an upper portion of the range of temperatures for applying tension to the sample as the temperature increases and said material contracts followed by relieving of tension as the temperature decreases and said material expands.

8. A method as claimed in claim 1 in which said material is a material which contracts as temperature increases and expands as temperature decreases, and which is engaged with said movable sample holding member for moving said movable sample holding member toward said fixed sample holding member as said material expands, and said step of mounting is carried out at a temperature in a lower portion of the range of temperatures for applying a tension to the sample as the temperature increases and said material contracts followed by relieving of tension as the temperature decreases and said material expands.

9. A method as claimed in claim 1 in which said material is a material which contracts as temperature increases and expands as temperature decreases, and which is engaged with said movable sample holding member for moving said movable sample holding member toward said fixed sample holding member as said material expands, and said step of mounting is carried out at a temperature in an upper portion of the range of temperatures for applying a compressive force to the sample as the temperature decreases and said material expands followed by relieving of compressive force as the temperature increases and said material contracts.

10. A method for carrying out a weathering test on a sample, comprising:

providing a sample holder having a pair of fixed sample holding members spaced from each other for holding respective ends of a sample to be tested, a force applying member for applying a lateral bending force to the sample to be tested, a force applying member mounting means on which said force applying member is movably mounted, said force applying member mounting means extending outwardly at an angle to a plane extending between said sample holding members, and a force applying means made of a material which is expandable and contractable by a predetermined amount with variations in temperature over a predetermined range and which is engaged with said force applying member mounting means;

mounting a sample in said holder by connecting respective ends of the sample to said sample holding members;

positioning said holder in an environment under weather conditions corresponding to those for which the sample is to be tested and including repeatedly varying temperature varying in a range of temperatures in which said force applying means expands and contracts for exposing said sample to said weather conditions while applying varying bending force to said sample by the expansion and contraction of said force applying means in accordance with the variations in temperature; and evaluating the weather-fastness of the thus tested sample.

11. A method as claimed in claim 10 in which said material is a material which expands as temperature increases and contracts as temperature decreases, and which is engaged with said movable force applying member mounting means for moving said force applying member away from said plane as said material expands, and said step of mounting is carried out at a temperature in an upper portion of the range of temperatures for applying a bending force to the sample as the temperature decreases and said material contracts followed by relieving the bending force as the temperature increases and said material expands.

12. A method as claimed in claim 10 in which said material is a material which contracts as temperature increases and expands as temperature decreases, and which is engaged with said movable force applying member mounting means for moving said force applying member toward said fixed sample holding member as said material contracts, and said step of mounting is carried out at a temperature in a lower portion of the range of temperatures for applying bending force to the sample held in said movable holding member as the temperature increases and said material contracts followed by relieving of the bending force as the temperature decreases and said material expands.

13. A sample holder for mounting a sample for a weather fastness test, comprising:
a fixed sample holding member for holding one end of a sample to be tested;
a movable sample holding member for holding the other end of the sample to be tested;
a movable sample holding member mounting means on which said movable sample holding member is movably mounted for movement toward and away from said fixed sample holding member; and
a force applying means made of a material which is expandable and contractable by a predetermined amount with a variation in temperature over a predetermined range, said force applying means being engaged with said movable sample holding member mounting means for moving said movable sample holding member to apply a force to the sample in accordance with the expansion and contraction of said force applying means as the temperature of the ambient environment in which said sample holder is present increases and decreases.

14. A sample holder as claimed in claim 13 in which said material is a material which expands as temperature increases and contracts as temperature decreases.

15. A sample holder as claimed in claim 13 in which said material is engaged with said movable sample holding member to move said movable sample holding member away from said fixed sample holding member as said material expands as temperature increases.

16. A sample holder as claimed in claim 14 in which said material is engaged with said movable sample holding member to move said movable sample holding member toward said fixed sample holding member as said material expands as temperature increases.

17. A sample holder as claimed in claim 13 in which said material is a material which contracts as temperature increases and expands as temperature decreases.

18. A sample holder as claimed in claim 17 in which said material is engaged with said movable sample holding member to move said movable sample holding member away from said fixed sample holding member as said material expands as temperature decreases.

19. A sample holder as claimed in claim 17 in which said material is engagaged with said movable sample holding member to move said movable sample holding member toward said fixed sample holding member as said material expands as temperature decreases.

20. A sample holder as claimed in any one of claims 13-19 in which said material is metal.

21. A sample holder as claimed in claim 20 in which said material is in the shape of a coil.

22. A sample holder as claimed in claim 21 in which said movable sample holding member mounting means comprise parallel rods mounted on one of said fixed sample holding members, and said movable sample holding member extends between said rods and is slidably mounted on said rods.

23. A sample holder as claimed in claim 22 in which said force applying means comprise metallic coils around said rods and having one end engaged with said movable sample holding member and the other end fixed to said holder.

24. A sample holder as claimed in claim 23 in which the other ends of said coils are fixed to said rods.

25. A sample holder for mounting a sample for a weather fastness test, comprising:
a pair of fixed sample holding members spaced from each other for holding respective ends of a sample to be tested;
a force applying member for applying a lateral bending force to the sample;
a force applying member mounting means on which said force applying member is movably mounted, said force applying member mounting means having an end secured to said holder and extending outwardly at an angle to a plane extending between said sample holding members, said force applying member being movable along said force applying member mounting means for movement toward and away from said plane between said fixed sample holding members; and
a force applying means made of a material which is expandable and contractable by a predetermined amount with a variation in temperature over a predetermined range, said force applying means being engaged with said force applying member for moving said force applying member along said force applying member mounting means to apply a lateral force to the sample in accordance with the expansion and contraction of said force applying means as the temperature of the ambient environment in which said sample holder is present increases and decreases.

26. A sample holder as claimed in claim 25 in which said material is a material which expands as temperature increases and contracts as temperature decreases.

27. A sample holder as claimed in claim 26 in which said material is engaged with said force applying member mounting means to move said force applying member away from said plane as said material expands as temperature increases.

28. A sample holder as claimed in claim 25 in which said material is a material which contracts as temperature increases and expands as temperature decreases.

29. A sample holder as claimed in claim 28 in which said material is engaged with said force applying member mounting means to move said force applying member away from said plane as said material expands as temperature decreases.

30. A sample holder as claimed in claim 25 in which said force applying member mounting means comprise parallel rods mounted on one of said fixed sample holding members, and said force applying member extends between said rods and is slidably mounted on said rods.

31. A sample holder as claimed in claim 30 in which said force applying means comprise metallic coils around said rods and having one end engaged with said force applying member mounting means and the other end fixed to said holder.

32. A sample holder as claimed in claim 31 in which the other ends of said coils are fixed to said rods.

* * * * *